US012274842B2

(12) United States Patent
Bonner et al.

(10) Patent No.: US 12,274,842 B2
(45) Date of Patent: Apr. 15, 2025

(54) GUIDE WIRE SYSTEM

(71) Applicant: Medtronic, Inc., Minneapolis, MN (US)

(72) Inventors: Matthew D. Bonner, Plymouth, MN (US); Kathryn E. Hilpisch, Cottage Grove, MN (US); Ronald A. Drake, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 423 days.

(21) Appl. No.: 17/805,450

(22) Filed: Jun. 3, 2022

(65) Prior Publication Data

US 2022/0387764 A1     Dec. 8, 2022

Related U.S. Application Data

(60) Provisional application No. 63/208,332, filed on Jun. 8, 2021.

(51) Int. Cl.
*A61M 25/09*     (2006.01)
*A61B 5/29*     (2021.01)
(Continued)

(52) U.S. Cl.
CPC ......... *A61M 25/09* (2013.01); *A61B 17/3468* (2013.01); *A61B 5/29* (2021.01);
(Continued)

(58) Field of Classification Search
CPC ........ A61M 25/09; A61M 2025/09183; A61M 25/09016; A61M 25/09025;
(Continued)

(56) References Cited

U.S. PATENT DOCUMENTS 3,814,104 A    6/1974   Irnich et al.
3,835,864 A    9/1974   Rasor et al.
(Continued)

FOREIGN PATENT DOCUMENTS

WO    2002022202 A2    3/2002
WO    2006118865 A2    11/2006
(Continued)

OTHER PUBLICATIONS

Austin et al., "Innovative pacing: Recent advances, emerging technologies, and future directions in cardiac pacing", Trends in Cardiovascular Medicine, vol. 26, Mayo Clinic Florida, 2016, pp. 452-463, (Applicant points out, in accordance with MPEP 609.04(a), that the year of publication, 2016, is sufficiently earlier than the effective U.S. filing date, so that the particular month of publication is not an issue.).

(Continued)

*Primary Examiner* — Tan-Uyen T Ho
*Assistant Examiner* — Khoa Tan Le
(74) *Attorney, Agent, or Firm* — Shumaker & Sieffert, P.A.

(57) ABSTRACT

A guide wire system configured to guide a medical device (e.g., a medical lead) to a target area within a patient. The guide wire system may be configured to penetrate and pass through a tissue wall in the patient to guide the medical device to the target area. The guide wire system includes a support section configured to expand to substantially maintain a position relative to the tissue wall. The guide wire system includes a pull wire configured to cause the support portion to expand. The expanded support section may provide counter-traction to a distal force on the tissue wall exerted by a medical device during, for example, fixation of the medical device to the target area, or other stages of an implantation. The support section is configured to re-estab- (Continued)

lish an initial configuration for proximal withdrawal from the tissue wall.

20 Claims, 8 Drawing Sheets

(51) Int. Cl.
*A61B 17/00* (2006.01)
*A61B 17/34* (2006.01)

(52) U.S. Cl.
CPC .............. *A61B 2017/00247* (2013.01); *A61B 2560/063* (2013.01); *A61M 2025/09183* (2013.01)

(58) Field of Classification Search
CPC .................. A61B 17/3468; A61B 5/29; A61B 2017/00247; A61B 2560/063; A61B 5/6851
See application file for complete search history.

(56) References Cited

U.S. PATENT DOCUMENTS

| | | | |
|---|---|---|---|
| 3,943,936 A | 3/1976 | Rasor et al. | |
| 4,103,690 A | 8/1978 | Harris | |
| 4,142,530 A | 3/1979 | Wittkampf | |
| 4,256,115 A | 3/1981 | Bilitch | |
| 4,269,198 A | 5/1981 | Stokes | |
| 4,280,512 A | 7/1981 | Karr et al. | |
| 4,858,623 A | 8/1989 | Bradshaw et al. | |
| 4,936,823 A | 6/1990 | Colvin | |
| 5,193,540 A | 3/1993 | Schulman et al. | |
| 5,411,535 A | 5/1995 | Fujii et al. | |
| 5,487,758 A | 1/1996 | Hoegnelid et al. | |
| 5,573,540 A | 11/1996 | Yoon | |
| 5,674,259 A | 10/1997 | Gray | |
| 5,683,447 A | 11/1997 | Bush et al. | |
| 6,007,558 A | 12/1999 | Ravenscroft et al. | |
| 6,151,525 A | 11/2000 | Soykan et al. | |
| 6,212,434 B1 | 4/2001 | Scheiner | |
| 6,240,322 B1 | 5/2001 | Peterfeso et al. | |
| 6,286,512 B1 | 9/2001 | Loeb et al. | |
| 6,409,674 B1 | 6/2002 | Brockway et al. | |
| 6,575,967 B1 | 6/2003 | Leveen et al. | |
| 6,643,546 B2 | 11/2003 | Mathis et al. | |
| 6,783,499 B2 | 8/2004 | Schwartz | |
| 6,915,149 B2 | 7/2005 | Ben-Haim | |
| 6,978,178 B2 | 12/2005 | Sommer et al. | |
| 7,082,335 B2 | 7/2006 | Klein et al. | |
| 7,139,614 B2 | 11/2006 | Scheiner et al. | |
| 7,290,743 B2 | 11/2007 | Nowack | |
| 7,412,289 B2 | 8/2008 | Malonek et al. | |
| 7,418,298 B2 | 8/2008 | Shiroff et al. | |
| 7,813,805 B1 | 10/2010 | Farazi | |
| 8,353,940 B2 | 1/2013 | Benderev | |
| 8,781,605 B2 | 7/2014 | Bornzin et al. | |
| 9,017,341 B2 | 4/2015 | Bornzin et al. | |
| 9,039,594 B2* | 5/2015 | Annest ................ | A61N 1/3956 607/9 |
| 9,597,514 B2 | 3/2017 | Khairkhahan et al. | |
| 9,901,732 B2 | 2/2018 | Sommer et al. | |
| 10,039,922 B2 | 8/2018 | Regnier | |
| 10,159,834 B2 | 12/2018 | Drake et al. | |
| 10,406,370 B1 | 9/2019 | Makharinsky | |
| 10,413,720 B2 | 9/2019 | Nuta et al. | |
| 10,493,284 B2 | 12/2019 | Ortega et al. | |
| 10,729,902 B1 | 8/2020 | Makharinsky et al. | |
| 10,792,080 B2 | 10/2020 | Raina et al. | |
| 11,331,475 B2 | 5/2022 | Drake et al. | |
| 2002/0103424 A1 | 8/2002 | Swoyer et al. | |
| 2002/0165589 A1 | 11/2002 | Imran et al. | |
| 2003/0060866 A1 | 3/2003 | Schmidt | |
| 2003/0088301 A1 | 5/2003 | King | |
| 2004/0122456 A1 | 6/2004 | Saadat et al. | |
| 2004/0147973 A1 | 7/2004 | Hauser | |
| 2004/0230281 A1 | 11/2004 | Heil et al. | |
| 2006/0084965 A1 | 4/2006 | Young | |
| 2006/0085039 A1 | 4/2006 | Hastings et al. | |
| 2006/0085041 A1 | 4/2006 | Hastings et al. | |
| 2006/0224224 A1 | 10/2006 | Muhlenberg et al. | |
| 2007/0179552 A1 | 8/2007 | Dennis et al. | |
| 2009/0082828 A1 | 3/2009 | Ostroff | |
| 2010/0145382 A1* | 6/2010 | Chanduszko ...... | A61B 17/0057 606/213 |
| 2010/0318172 A1 | 12/2010 | Schaefer | |
| 2012/0172892 A1 | 7/2012 | Grubac et al. | |
| 2014/0039591 A1 | 2/2014 | Drasler et al. | |
| 2014/0066895 A1 | 3/2014 | Kipperman | |
| 2014/0107723 A1 | 4/2014 | Hou et al. | |
| 2015/0039070 A1 | 2/2015 | Kuhn et al. | |
| 2015/0335894 A1 | 11/2015 | Bornzin et al. | |
| 2017/0326369 A1 | 11/2017 | Koop et al. | |
| 2018/0050208 A1 | 2/2018 | Shuros et al. | |
| 2019/0083779 A1 | 3/2019 | Yang et al. | |
| 2019/0111265 A1 | 4/2019 | Zhou | |
| 2019/0111270 A1 | 4/2019 | Zhou | |
| 2019/0143118 A1 | 5/2019 | Bullinga | |
| 2019/0192863 A1 | 6/2019 | Koop et al. | |
| 2019/0209845 A1 | 7/2019 | Stadler et al. | |
| 2019/0232053 A1 | 8/2019 | Yang et al. | |
| 2019/0269420 A1 | 9/2019 | Matusaitis et al. | |
| 2019/0351236 A1 | 11/2019 | Koop | |
| 2019/0374254 A1 | 12/2019 | Arevalos et al. | |
| 2020/0229805 A1 | 7/2020 | Gammie et al. | |
| 2020/0229806 A1 | 7/2020 | Goldfarb et al. | |
| 2020/0261725 A1 | 8/2020 | Yang et al. | |
| 2020/0261734 A1 | 8/2020 | Yang et al. | |
| 2020/0289829 A1 | 9/2020 | Ghosh | |
| 2020/0306522 A1 | 10/2020 | Chen et al. | |
| 2020/0306530 A1 | 10/2020 | Koop et al. | |
| 2020/0353249 A1 | 11/2020 | Min et al. | |
| 2020/0353265 A1 | 11/2020 | Ghosh et al. | |
| 2020/0398045 A1 | 12/2020 | Anderson et al. | |
| 2021/0046306 A1 | 2/2021 | Grubac et al. | |
| 2021/0187307 A1 | 6/2021 | Ries et al. | |
| 2023/0012417 A1 | 1/2023 | Rock et al. | |

FOREIGN PATENT DOCUMENTS

| | | |
|---|---|---|
| WO | 2018097826 A1 | 5/2018 |
| WO | 2020023406 A1 | 1/2020 |
| WO | 2020076833 A1 | 4/2020 |
| WO | 2020163031 A1 | 8/2020 |

OTHER PUBLICATIONS

Haqqani et al., "The Implantable Cardioverter-Defibrillator Lead: Principles, Progress and Promises," Pace, vol. 32, Oct. 2009, pp. 1336-1353.

Mulpuru et al., "Cardiac Pacemakers: Functions, Troubleshooting, and Management", Journal of the American College of Cardiology, vol. 69, No. 2, Oct. 18, 2016, pp. 189-210.

Prosecution History from U.S. Appl. No. 17/191,071, dated Jun. 9, 2022 through Jul. 31, 2023, 34 pp.

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.

Tjong et al., "The modular cardiac rhythm management system: the Empower leadless pacemaker and the Emblem subcutaneous ICD," Herzschrittmachertherapie + Elektrophysiologie, vol. 29, Oct. 31, 2018, pp. 355-361.

Hayes, "Advances in pacing therapy for bradycardia", International Journal of Cardiology, vol. 32, Elsevier Science Publishers B.V., Apr. 1, 1991, pp. 183-196.

Petrie, "Permanent Transvenous Cardiac Pacing", Clinical Techniques in Small Animal Practice, Elsevier Inc., 2005, pp. 164-172, (Applicant points out, in accordance with MPEP 609.04(a), that the

(56) References Cited

OTHER PUBLICATIONS year of publication, 2005, is sufficiently earlier than the effective U.S. filing date, so that the particular month of publication is not an issue.).

U.S. Appl. No. 17/653,959, filed Mar. 8, 2022, naming inventors Matthew D. Bonner et al.

* cited by examiner

GUIDE WIRE SYSTEM

This application claims the benefit of U.S. Provisional Application Ser. No. 63/208,332 (filed Jun. 8, 2021), which is entitled "GUIDE WIRE SYSTEM" and is incorporated by reference herein in its entirety.

TECHNICAL FIELD

This disclosure is related to a guide wire for implantable medical systems

BACKGROUND

Various types of implantable medical leads have been implanted for treating or monitoring one or more conditions of a patient. Such implantable medical leads may be adapted to allow medical devices to monitor or treat conditions or functions relating to heart, muscle, nerve, brain, stomach, endocrine organs or other organs and their related functions. Implantable medical leads include electrodes and/or other elements for physiological sensing and/or therapy delivery. Implantable medical leads allow the sensing/therapy elements to be positioned at one or more target locations for those functions, while the medical devices electrically coupled to those elements via the leads are at different locations.

Implantable medical leads, e.g., distal portions of elongated implantable medical leads, may be implanted at target locations selected to detect a physiological condition of the patient and/or deliver one or more therapies. For example, implantable medical leads may be delivered to a target location within an atrium or ventricle to sense intrinsic cardiac signals and deliver pacing or antitachyarrhythmia shock therapy from a medical device coupled to the lead. The implantable medical lead may be configured to translate over a guide wire to navigate the implantable lead to the target location.

SUMMARY

In an example, a guide wire system comprises: an elongated body defining a proximal portion, a support portion, a distal portion, and a distal tip at a distal end; wherein the elongated body includes a body wall defining an inner lumen within at least the support portion, wherein the elongated body defines at least two slits extending through the wall in the support portion and the elongated body defines an expansion member between the two slits, and wherein the distal tip is configured to penetrate a tissue wall; and a pull wire configured to exert a proximal force on the distal portion of the elongated body when the proximal force is exerted on the pull wire, wherein the expansion member is configured to expand radially outward from the inner lumen when the proximal force is exerted on the distal portion.

In an example, a guide wire system comprises: an elongated body defining a proximal portion, a support portion, a distal portion, and a distal tip at a distal end; wherein the elongated body includes a body wall defining an inner lumen within the support portion, wherein the elongated body defines a longitudinal axis extending within the inner lumen at least through the support portion, wherein the elongated body defines at least two slits substantially parallel to the longitudinal axis and extending through the wall in the support portion and the elongated body defines an expansion member between the two slits, and wherein the distal tip is configured to penetrate a tissue wall; and a pull wire configured to exert a proximal force on the distal portion of the elongated body when the proximal force is exerted on the pull wire, wherein the expansion member is configured to expand radially outward from the inner lumen when the proximal force is exerted on the distal portion, and wherein the expansion member is resiliently biased to displace toward the inner lumen when the proximal force exerted by the pull wire decreases.

In examples, a method comprises: exerting, using a pull wire, a force in a proximal direction on a distal portion of an elongated body comprising a proximal portion, and support portion, the distal portion, and a distal tip configured to penetrate a tissue wall at a distal end; and radially expanding, using the force on the distal portion, an expansion member defined between at least two slits extending through a wall of the elongated body, wherein the wall defines an inner lumen within the support portion.

The details of one or more examples are set forth in the accompanying drawings and the description below. Other features, objects, and advantages will be apparent from the description and drawings, and from the claims.

DETAILED DESCRIPTION

Figure 1:
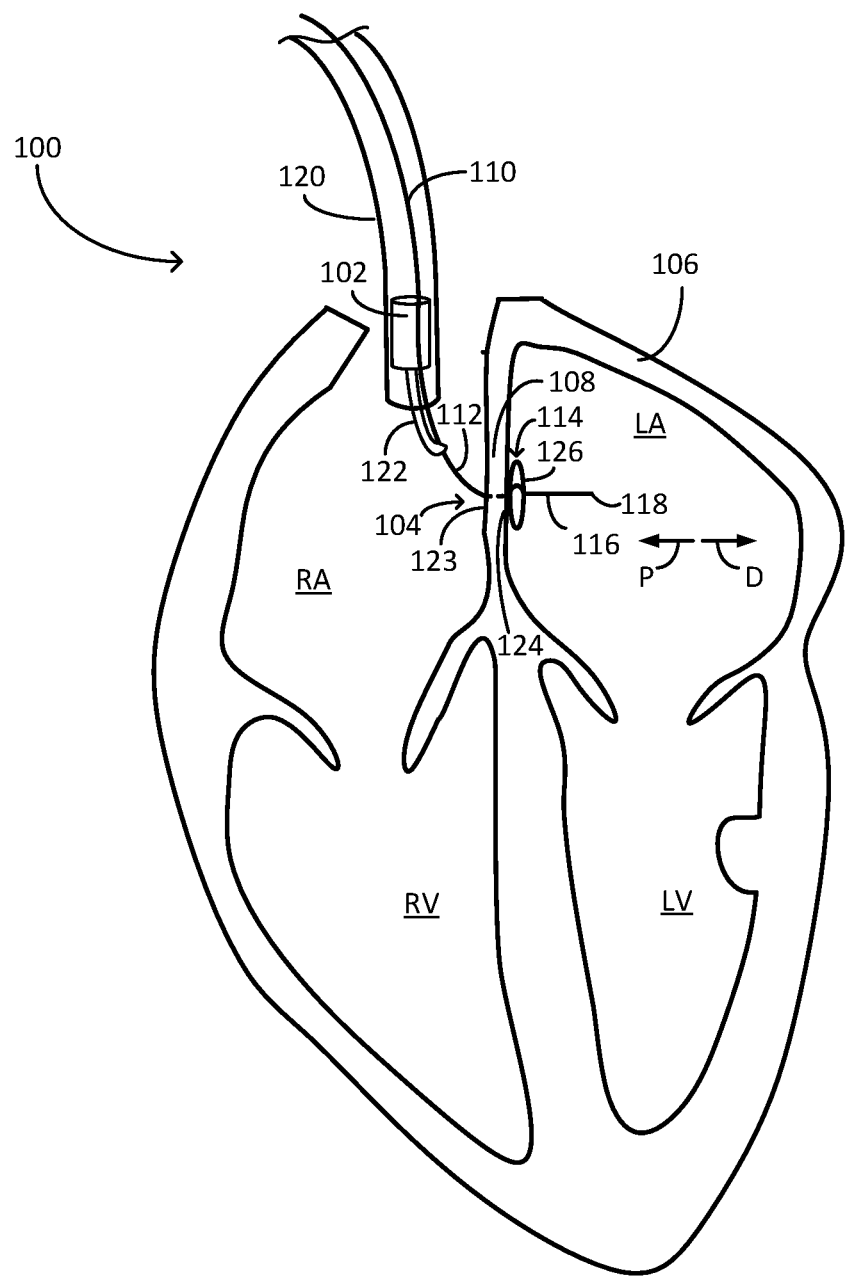
FIG. 1 is a conceptual diagram illustrating an example guide wire system.

This disclosure describes a guide wire system configured to guide a medical device (e.g., a medical lead) to a target area within a patient. The guide wire system may be configured to penetrate and pass through a tissue wall in the patient to guide the medical device to the target area. The guide wire system is configured to substantially maintain its position relative to the tissue wall when a proximal force is applied to the guide wire system (e.g., by a clinician). In examples, the guide wire system is configured to transfer some portion of the proximal force to the tissue wall. The proximal force transferred to the tissue wall may provide counter-traction to a distal force on the tissue wall exerted by a medical device during, for example, fixation of the medical device to the target area, or other stages of an implantation.

In examples, the guidewire system is configured to guide a medical device to a target location within a chamber of a heart, such as a right atrium (RA), right ventricle (RV), left atrium (LA), and/or left ventricle (LV). The guide wire system may be configured to penetrate a tissue wall (e.g., a septum) separating a first chamber from a second chamber, such that a proximal portion remains in the first chamber while a support portion extends into the second chamber. The guidewire system is configured to cause the support portion to radially expand within the second chamber. The expansion causes the support portion to contact a surface of the tissue wall to minimize and/or prevent a proximal translation of the guide wire system (e.g., a "backing out") when a proximal force is applied to the guidewire system, such that the guide wire system remains in place relative to the tissue wall. The support portion may be configured to substantially provide support to the tissue wall to provide counter-traction to the tissue wall. For example, when a clinician exerts a distal force on a first side of a septum to, for example, anchor or implant a medical device (e.g., a medical lead) to or within the septum, the clinician may exert a proximal force on the guidewire system to cause the support portion to exert a proximal force on a second side of the tissue wall, such that the guidewire provides a measure of counter-traction to the distal force transmitted by the medical device. The guide wire system is configured such that relaxing the proximal force causes the support portion to collapse, such that the guide wire system may be withdrawn substantially atraumatically back through the septum. In some examples, the guide wire system is configured such that relaxing the proximal force and withdrawing at least the support portion back through the septum causes the support portion to collapse, such that the guide wire system may be withdrawn substantially atraumatically back through the septum.

The guide wire system includes an elongated body such as a tubular guide wire configured to pass through a device lumen defined by a medical device. The elongated body includes a proximal portion, a support portion, and a distal portion including a distal tip at a distal end. The distal tip is configured to penetrate a tissue wall, such as a cardiac septum. The elongated body is configured to receive a distal force to cause the distal tip to penetrate the tissue wall from a first side of the tissue wall (e.g., a septal wall in an RA, RV, LA, or LV) and exit through a second side of the tissue wall. The guide wire is configured such that the distal portion and the support portion may likewise pass from the first side to the second side, such that the tissue wall is positioned between the proximal portion (e.g., located in an RA or RV) and the support portion, the distal portion, and the distal tip (e.g., located in an LA or LV).

The guide wire system includes a pull wire configured to cause the support portion to expand radially outward. The support portion is configured to expand radially outward to an expanded dimension greater than a dimension of the tissue wall puncture generated by the distal tip, such that a proximal force exerted on the guidewire system causes the expanded support portion to contact the tissue wall rather than translate proximally through the tissue wall puncture. In examples, the support portion is configured to establish an initial dimension (e.g., a diameter) in a relaxed condition and establish the expanded dimension in an expanded condition, with the expanded dimension greater than the initial dimension. For example, the support portion may be configured such that the expanded dimension is two times, five times, ten times, or some other multiple greater than the initial dimension. The guide wire system may be configured such that the distal tip causes a tissue wall puncture with a dimension substantially equal to the initial dimension, such that the expanded dimension of the expanded support portion substantially prevents the expanded support portion, the distal portion, and the distal tip from passing proximally through (e.g., backing out of) the tissue wall puncture.

The elongated body including the proximal portion, the support portion, the distal portion, and the distal tip includes a wall defining an inner lumen within at least the support portion. The elongated body defines at least two slits extending through the wall from an exterior surface of the elongated body to the inner lumen. The elongated body defines an expansion member between the at least two slits. In examples, the elongated body defines a longitudinal axis through the inner lumen, and the expansion member is substantially parallel to the longitudinal axis. In examples, one or more of the at least two slits is substantially parallel to the longitudinal axis. The elongated body may define any number of slits and expansion members. In examples, the elongated body defines a plurality of expansion members (e.g., two, three, four, or more), with each expansion member between a first longitudinal slit and a second longitudinal slit of the at least two slits.

As discussed, the support portion is between the distal portion of the elongated body and the distal portion of the elongated body. The support portion is configured such that a proximal force exerted on the distal portion causes the expansion member of the support portion to expand radially outward away from the longitudinal axis of the inner lumen. In examples, the proximal force causes the distal portion to displace toward the proximal portion in a direction along the longitudinal axis. The displacement may substantially place the expansion member in compression, causing the expansion member to buckle in a direction away from the inner lumen. The buckling of the expansion member may substantially define the expanded dimension of the support portion. In examples wherein the elongated body defines a plurality of expansion members, each expansion member may buckle outwards in a different radial direction from to the longitudinal axis, such that the expanded support portion acts to spread a proximal force (e.g., a counter-traction force) over a substantially circumferential area around the tissue wall puncture created by the distal tip.

The guide wire system includes a pull wire configured to exert the proximal force on the distal portion to cause expansion of the support portion. The pull wire may be configured to extend outside a patient, such that a clinician may cause the pull wire to exert the proximal force and cause the expansion. In examples, the pull wire is configured to translate within the inner lumen defined by the elongated body. In some examples, the elongated body further defines the inner lumen within some portion of or substantially all of the proximal portion of the elongated body. In some examples, the elongated body defines an opening to the lumen substantially at a proximal end of the elongated body, and a proximal end of the pull wire extends through the lumen opening.

FIG. 1 is a conceptual diagram illustrating an example guide wire system 100 guiding a medical device 102 toward a target area 104 in a heart 106 of a patient. Heart 106 includes a right atrium (RA), left atrium (LA), right ventricle (RV), and left ventricle (LV). A tissue wall 108 (e.g., a cardiac septum) separates the RA and LA. Guide wire system 100 includes an elongated body 110 defining a proximal portion 112, an expanded support portion 114, a distal portion 116, and a distal tip 118. In FIG. 1, a portion of guide wire system 100 and medical device 102 are positioned within a catheter lumen defined by a delivery catheter 120. Proximal portion 112 extends through a device lumen of a lead 122 of medical device 102. Medical device 102 is configured translate through the catheter lumen along proximal portion 112 such that medical device 102 may be positioned in proximity to target area 104.

FIG. 1 illustrates guide wire system 100 penetrating tissue wall 108 and extending from a first chamber (e.g., the RA) to a second chamber (e.g., the LA) of heart 106. Guide wire system 100 is configured such that a distal force (e.g., in the distal direction D) on elongated body 110 may cause distal tip 118 to penetrate tissue wall 108. In examples, guide wire system 100 includes an inner sheath 186 (FIG. 5A) defining a lumen configured to guide and/or support elongated body 110 as distal tip 110 penetrates tissue wall 108. In examples, inner sheath 186 is configured to engage tissue wall 108 (e.g., using one or more fixation barbs, tines, or other structures) to guide, support, and/or assist distal tip 118 in the penetration of tissue wall 108. In examples, inner sheath 186 is configured to be relatively stiff (e.g., have a stiffness) to guide, support, and/or assist distal tip 110 in the penetration of tissue wall 108.

Guide wire system 100 is configured such that at least distal portion 116 and support portion 114 may translate through a tissue wall puncture substantially formed by distal tip 118 when distal tip 118 penetrates tissue wall 108, such that distal portion 116 and support portion 114 reside in the second chamber (e.g., the LA) as proximal portion 112 remains in the first chamber (e.g., the RA). Distal tip 118 may be configured to penetrate a first tissue surface 123 of tissue wall 108 and exit through a second tissue surface 124 opposite first tissue surface 123. Although illustrated in FIG. 1 in an expanded condition, and as will be discussed, support portion 114 is configured to establish a cross-section largely uniform with distal portion 116 in a relaxed condition, such that support portion 114 may pass from the first chamber to the second chamber through the tissue wall puncture formed by distal tip 118.

Guide wire system 100 is configured to cause support portion 114 to radially expand outward to define an expanded dimension greater than a dimension of the tissue wall puncture formed by distal tip 118. The expanded dimension may define, for example, a radial dimension from a longitudinal axis of guide wire system 100 greater than a radial dimension of distal portion 116. The expanded dimension may act to minimize and/or prevent a proximal translation of support portion 114, distal portion 116, and distal tip 118 when support portion 114 is expanded. For example, when a proximal force (e.g., in the proximal direction P) is applied to elongated body 110, the expanded support portion 114 may act against second tissue surface 124 to substantially prevent proximal translation of guide wire system 100 relative to tissue wall 108. Guide wire system 100 is configured such that a clinician may control the expansion of support portion 114 using a pull wire (not shown), such that the clinician may cause support portion 114 to pass through tissue wall 108 in a relaxed condition (e.g., defining a cross-section substantially uniform to distal portion 116) prior to causing the expansion of support portion 114. Inner sheath 186 (FIG. 5A) guiding and/or supporting elongated body 110 may be configured to be removed (e.g., by a clinician) from heart 106 once distal tip 118 has penetrated tissue wall 108 and/or support portion 114 has radially expanded outward.

Support portion 114 may be configured to substantially provide support to tissue wall 108 to provide counter-traction to tissue wall 108. For example, when medical device 102 reaches target area 104, medical device 102 may be caused (e.g., by a clinician) to exert a distal force on tissue wall 108 as lead 122 enters tissue wall 108 and/or medical device 102 is fixated to tissue wall 108. A proximal force on guide wire system 100 (e.g., exerted by the clinician) may cause support portion 114 to exert a proximal force on second tissue surface 124, such that the guidewire provides a measure of counter-traction to the distal force exerted by medical device 102. Guide wire system 100 is configured such that support portion 114 may relax from the expanded condition to define a cross-section substantially uniform to distal portion 116, such that guide wire system 100 may be withdrawn substantially atraumatically back through tissue wall 108 once medical system 102 is positioned, or for other reasons.

Elongated body 110 defines one or more expansion members such as expansion member 126 configured to expand radially outward to define the expanded dimension of support portion 114. In examples, expansion member 126 is reliantly biased such that support portion 114 defines a cross-section substantially uniform to distal portion 116 when expansion member 126 is in a substantially relaxed (e.g., zero stress) condition. Expansion member 126 may be configured to buckle outward to define the expanded dimension of support portion 114 when placed under a compressive stress. For example, expansion member 126 may be configured to buckle outward when distal portion 116 is caused to translate toward proximal section 112 to place expansion member 126 in compression, such that expansion member 126 defines the expanded dimension. In some examples, expansion member 126 may be resiliently biased such that, when the compression is relaxed (e.g., when distal portion 116 is allowed to translate away from proximal portion 112), expansion member 126 displaces inward to cause support portion 114 to define the cross-section substantially uniform to distal portion 116.

Guide wire system 100 includes a pull wire configured to cause expansion member 126 to define the expanded dimension. In examples, the pull wire is configured to exert a proximal force on distal portion 116 to cause distal portion 116 to compress support portion 114 and cause expansion member 126 to buckle outward. The pull wire is configured to allow a clinician to exert a proximal force on the pull wire to cause the pull wire to exert the proximal force on distal portion 116, such that the clinician may control the expansion of support portion 114. Guide wire system 100 may be configured such that, when the proximal force exerted by the pull wire is reduced and support portion 114 is withdrawn proximally (e.g., by a clinician) through tissue wall 108 (e.g., through the tissue wall puncture substantially formed by distal tip 118), tissue wall 108 may cause expansion member 126 and/or support portion 114 to substantially collapse from the expanded dimension, such that expansion member 126 and/or support portion 114 define a cross-section similar to distal portion 116. Guide wire system 100 may be configured such that, when the proximal force exerted by the pull wire is reduced, the resilient biasing of expansion member 114 causes expansion member 114 to displace inward. Guide wire system 100 may be configured such that, when the proximal force exerted by the pull wire substantially ceases, the resilient biasing of expansion member 14 causes support portion 114 to define the cross-section substantially uniform to distal portion 116.

Guide wire system 100 may be configured such that one or more portions of elongated body 110 are steerable by a clinician. Elongated body 110 may be a substantially flexible body configured to be steered through vasculature and other portions of a patient. In examples, elongated body 110 is configured such that a first portion of elongated body 110 (e.g., proximal portion 116) may define a first curvature relative to a set of reference axes and a second portion (e.g., support portion 114 and/or distal portion 116) may define a second curvature relative to the set of references axes, with the first curvature different than the first curvature. In examples, elongated body 110 is configured to define the first curvature in a first plane and the second curvature in a second plane rotated at least 30 degrees relative to each axis in the reference axes. The pull wire of guide wire system 100 may be configured to exert the proximal force on distal portion 116 when elongated body 110 defines the first curvature and/or the second curvature.

Figure 2:
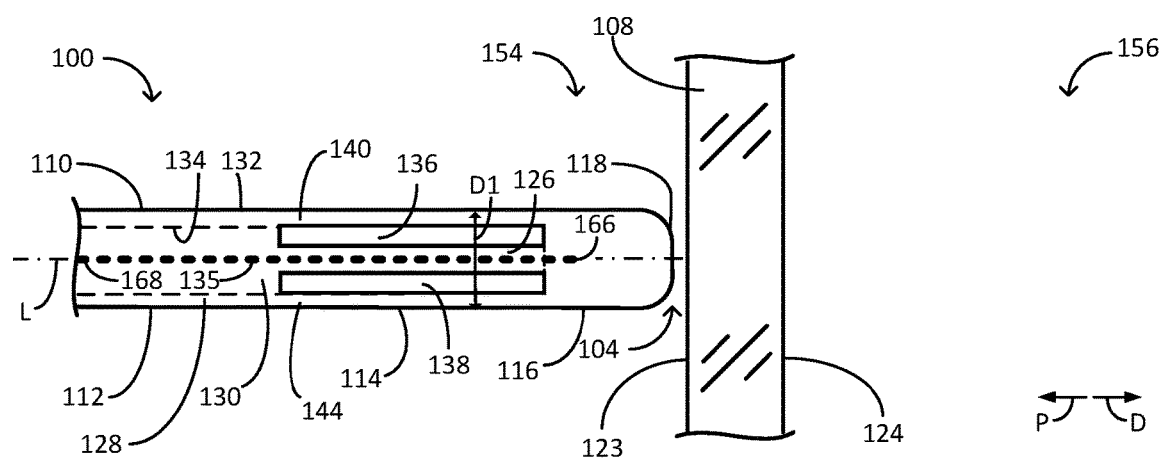
FIG. 2 is a conceptual diagram illustrating a proximal portion, a support portion, and a distal portion of an example guide wire system.
Figure 3:
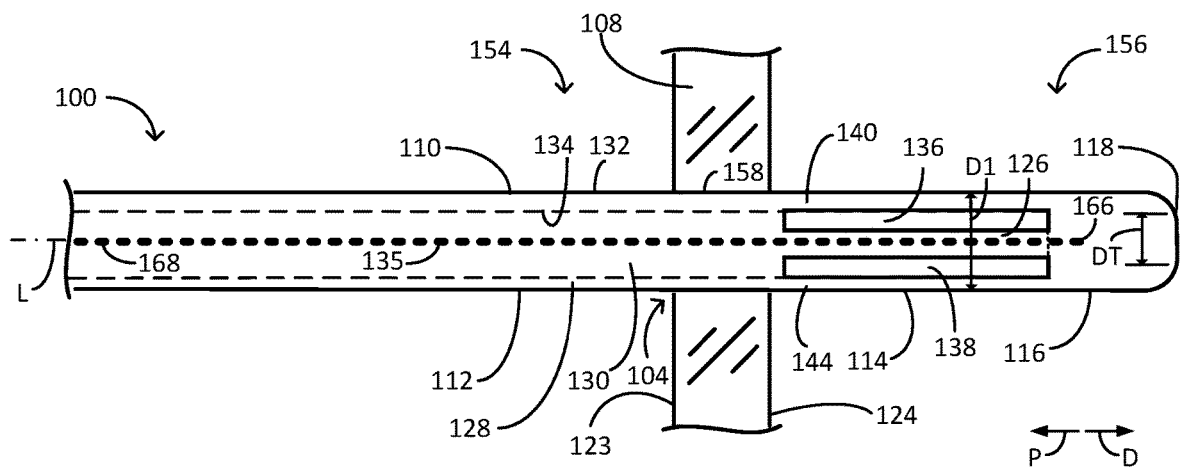
FIG. 3 is a conceptual diagram illustrating the guide wire system of FIG. 2 penetrating a tissue wall.
Figure 4:
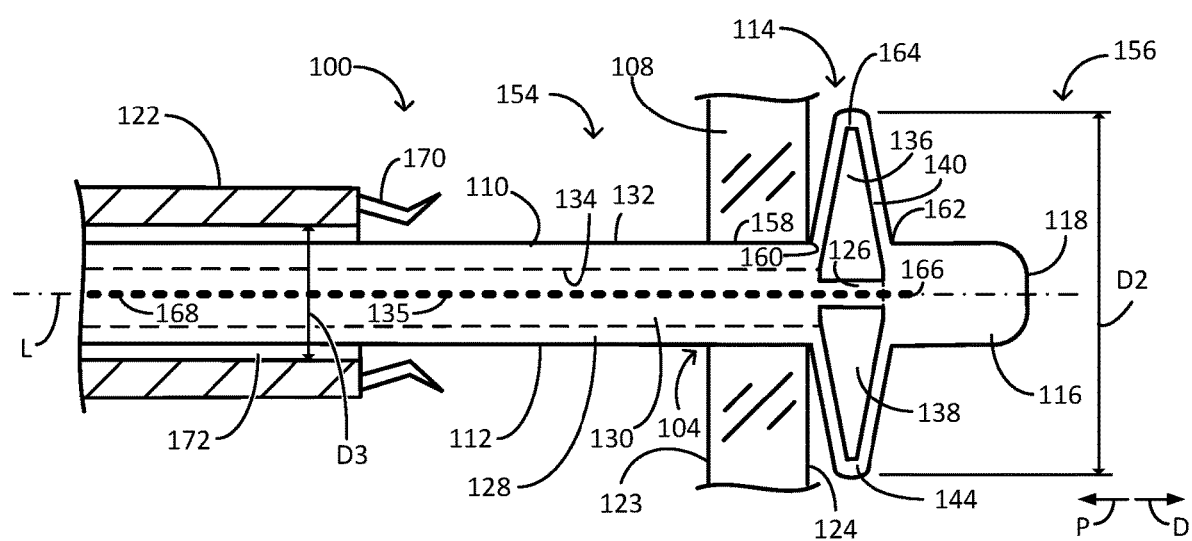
FIG. 4 is a conceptual diagram illustrated the support section of the guide wire system of FIG. 2 and FIG. 3 in an expanded configuration.
Figure 5B:
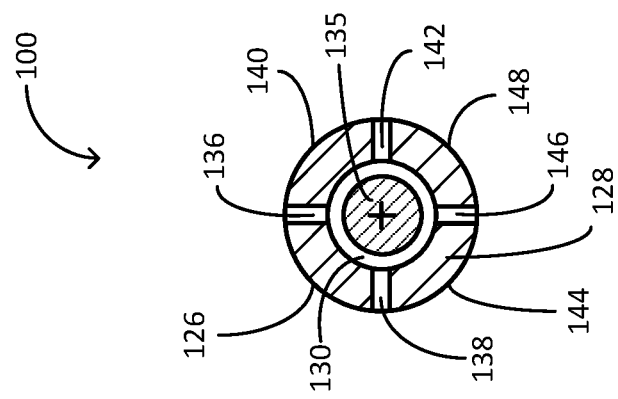
FIG. 5B is a is a cross-sectional view relative to a second cutting plane illustrating a pull wire within an inner lumen of the guide wire system of FIG. 5A.
Figure 5A:
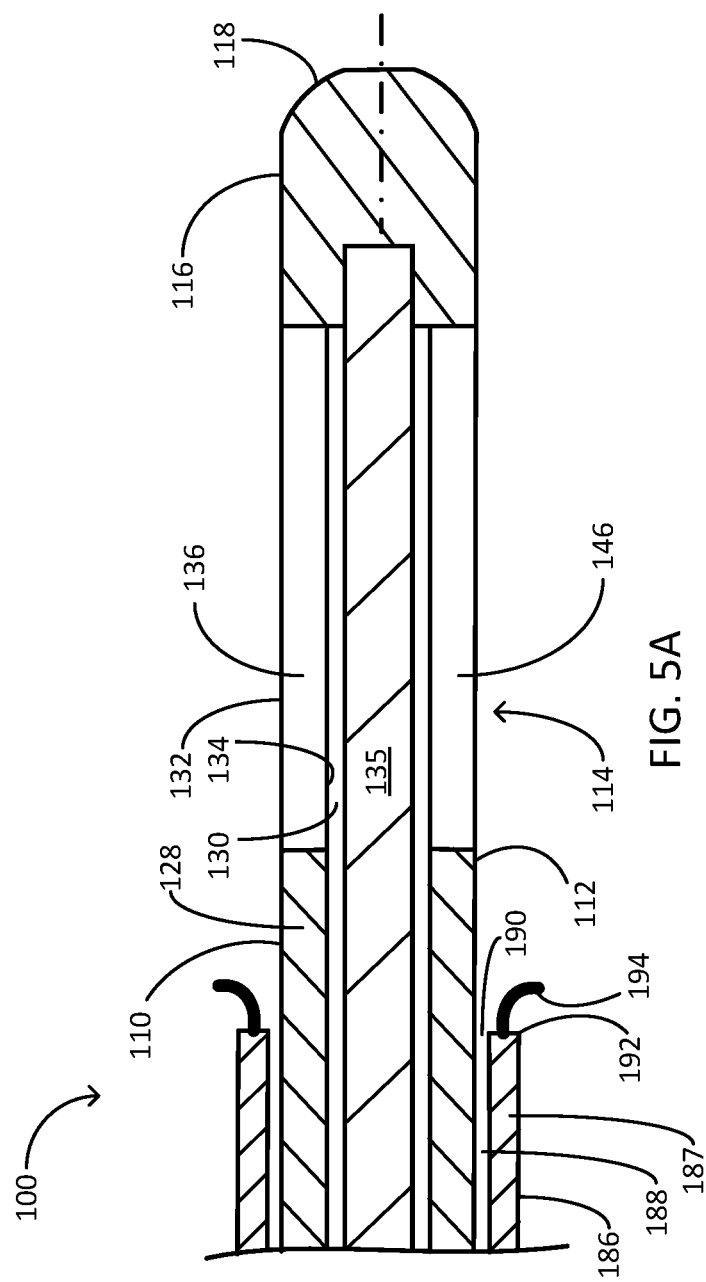
FIG. 5A is a cross-sectional view relative to a first cutting plane illustrating a pull wire within an inner lumen of a guide wire system.
Figure 6B:
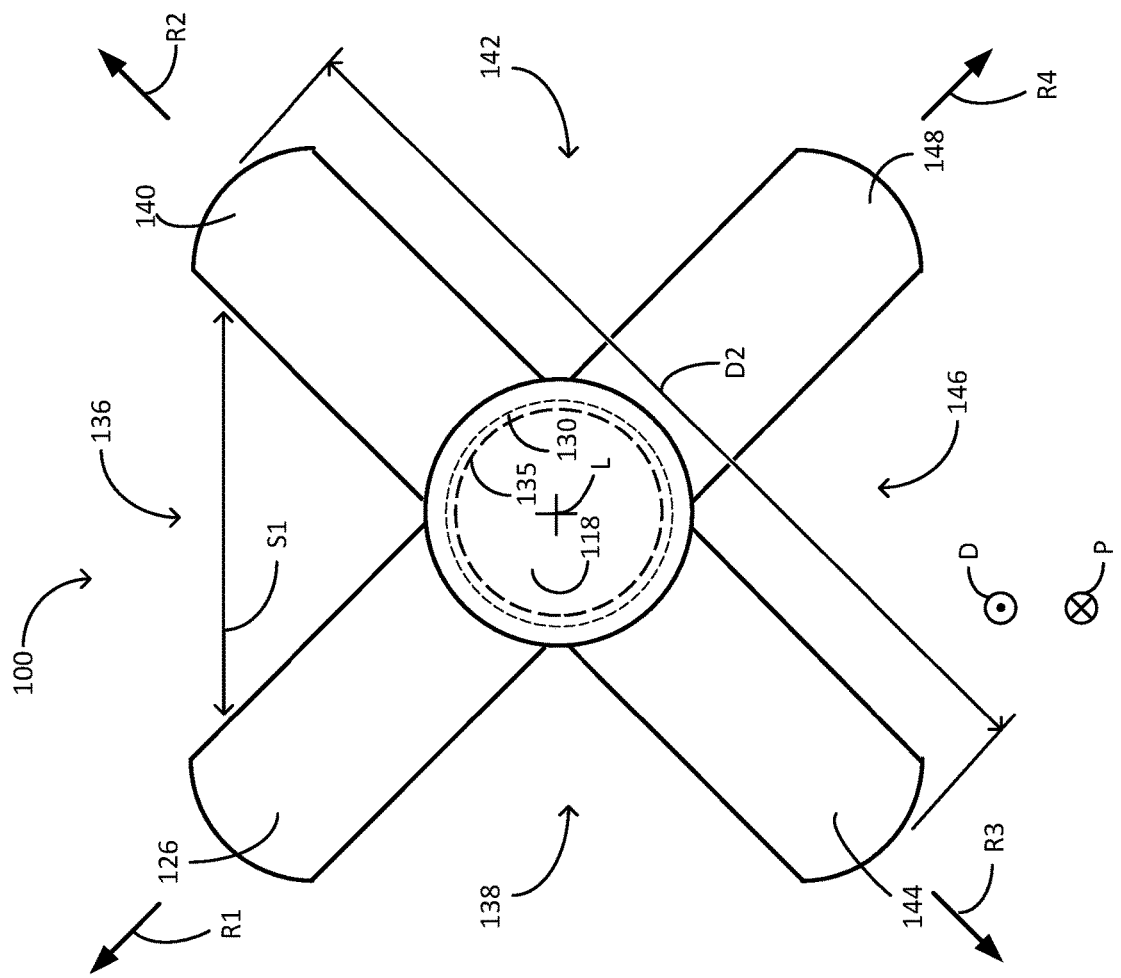
FIG. 6B is a conceptual diagram of the support section of FIG. 6A defining and expanded dimension.
Figure 6A:
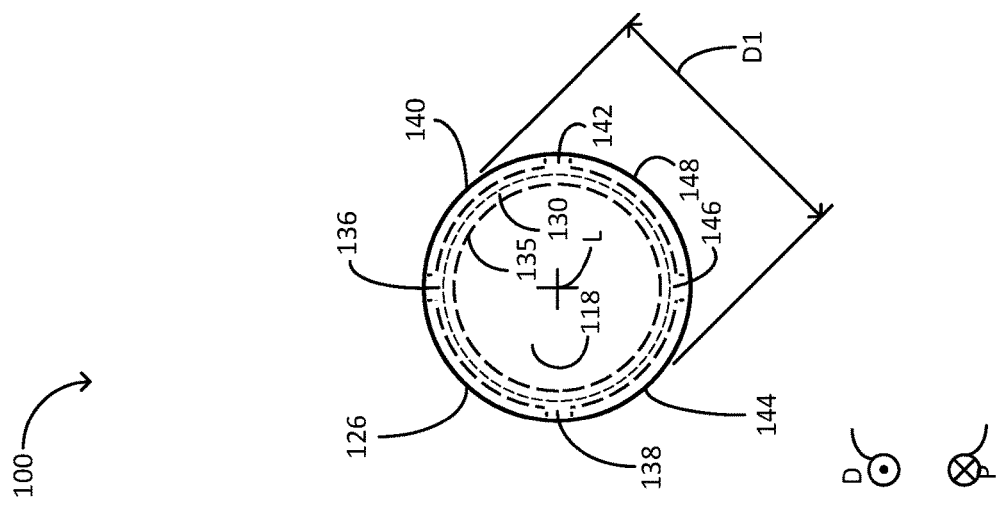
FIG. 6A is a conceptual diagram of a support section defining an initial dimension.

FIG. 2, FIG. 3, and FIG. 4 illustrate an example guide wire system 100 configured to penetrate a tissue wall 108. Guide wire system 100 includes proximal portion 112, support portion 114, and distal portion 116 defining distal tip 118. FIG. 5A illustrates a cross-section of guide wire system 100 of FIG. 1, FIG. 2, FIG. 3, and FIG. 4 with a cutting plane parallel to a longitudinal axis L defined by guide wire system 100. FIG. 5B illustrates a cross-section of guide wire system 100 of FIG. 2, FIG. 3, and FIG. 4 with a cutting plane perpendicular to the longitudinal axis L. FIG. 6A illustrates an end-view of an example guide wire system with support portion 114 in a relaxed condition. FIG. 6B illustrates the example guide wire system of FIG. 6A with support portion 114 in the expanded condition.

Referring to FIG. 2, elongated body 110 includes a wall 128 defining an inner lumen 130. Inner lumen 130 extends at least through support portion 114, and may extend through some or substantially all of proximal portion 112 and distal portion 116. In examples, wall 128 includes an exterior surface 132 and an interior surface 134 (illustrated with dashed lines) opposite exterior surface 132, and interior surface 134 defines inner lumen 130. In examples, at least some portion of elongated body 110 is a tubular body defining a substantially circular circumference around exterior surface 132. At least a portion of inner lumen 130 may define a substantially circular circumference around interior surface 134. Guide wire system 100 includes a pull wire 135 (illustrated with dashed line) configured to exert a proximal force (e.g., in the proximal direction P) on distal portion 116. In examples, pull wire 135 extends through inner lumen 130, although this is not required.

Elongated body 110 defines at least two slits such as a first slit 136 and a second slit 138. First slit 136 and second slit 138 extend through wall 128. In examples, first slit 136 and second slit 138 each define a passage fluidly coupling exterior surface 132 and interior surface 134. Elongated body 110 defines expansion member 126 between first slit 136 and second slit 138. Elongated body 110 may include any number of slits and define any number of expansion members. For example, elongated body 110 may define an expansion member 140 between first slit 136 and a third slit 142 (FIG. 5A, 5B). Elongated body 110 may define an expansion member 144 between second slit 138 and a fourth slit 146, and may define an expansion member 148 between third slit 142 and fourth slit 146.

First slit 136, second slit 138, third slit 142, and/or fourth slit 146 may define any width across the respective slit sufficient to define an expansion member as defined here. In examples, first slit 136, second slit 138, third slit 142, and/or fourth slit 146 define a width less than 0.1 inches, in other examples less than 0.01 inches, and in other examples less than 0.005 inches. Wall 128 may have any thickness. In examples, wall 128 defines a thickness from exterior surface 132 to interior surface 134 of less than 0.2 inches, in other examples less than 0.05 inches, and in other examples less than 0.025 inches. Expansion member 126, expansion member 140, expansion member 144, and/or expansion member 148 may define any length. In examples, expansion member 126, expansion member 140, expansion member 144, and/or expansion member 148 define a length substantially parallel to longitudinal axis L of less than 5.0 inches, in other examples less than 2.0 inches, and in other examples less than 0.6 inches.

Support portion 114 is configured to define an initial dimension D1 (e.g., a diameter) when expansion members 126, 140, 144, 148 are in a relaxed, substantially zero-stress condition. In examples, expansion members 126, 140, 144, 148 are configured to define the initial dimension D1 in the absence of a proximal force exerted on distal portion 116 by pull wire 135 when expansion members 126, 140, 144, 148 are withdrawn proximally (e.g., by a clinician) through tissue wall 108 (e.g., through the tissue wall puncture substantially formed by distal tip 118). In some examples, expansion members 126, 140, 144, 148 may be resiliently biased to cause support portion 114 to define the initial dimension D1. Expansion members 126, 140, 144, 148 may be configured to cause support portion 114 to define the initial dimension D1 in the substantial absence of compressive forces on expansion members 126, 140, 144, 148 (e.g., a compressive force exerted as a result of distal portion 116 displacing towards proximal portion 112). Expansion member 126, 140, 144, 148 may be configured to elastically deform and buckle outward when subject to a compressive force. Expansion member 126, 140, 144, 148 may be resiliently biased to substantially re-establish the initial dimension D1 when the compressive force is removed. In examples, elongated body 110 is configured such that proximal portion 112 and/or distal portion 116 define a cross-sectional dimension (e.g., a dimension perpendicular to longitudinal axis L) substantially equal (e.g., within 1%, 10%, or 20%) to the initial dimension D1.

As illustrated in FIG. 3, guide wire system 100 is configured such that a distal force (e.g., in the distal direction D) on elongated body 110 causes distal tip 118 to penetrate first tissue surface 123 of tissue wall 108 and exit through second tissue surface 124 opposite first tissue surface 123. First tissue surface 123 may be a tissue surface in a first chamber 154 (e.g., the RA, LA, RV, or LV) of heart 106. Second tissue surface 124 may be a tissue surface in a second chamber 156 (e.g., the RA, LA, RV, or LV) of heart 106. Guide wire system 100 is configured such that at least distal portion 116 and support portion 114 may translate through tissue wall 108 into second chamber 156. In examples, distal tip 118 is configured to cause a tissue wall puncture 158 through tissue wall 108, and at least distal portion 116 and support portion 114 are configured to pass through tissue wall 108 through tissue wall puncture 158.

Guide wire system 100 may include an inner sheath 186 (FIG. 5A) defining an inner sheath lumen 188 configured to guide and/or support elongated body 110 as distal tip 118 penetrates tissue wall 108. Inner sheath 186 may include one or fixation elements 194 configured to engage tissue wall 108 to guide, support, and/or assist distal tip 118 in the penetration of tissue wall 108. In examples, inner sheath 186 includes a sheath body 187 defining a sheath lumen 188. Sheath body 187 may define a lumen opening 190 configured to open into sheath lumen 188. In examples, sheath body 187 defines lumen opening 190 substantially at a distal end 192 of sheath body 187. In examples, at least some portion of elongated body 110 (e.g., support structure 114, distal portion 116, and/or distal tip 118) may be configured to slidably translate (e.g., proximally or distally) within sheath lumen 188 and/or pass through lumen opening 190. In some examples, sheath body 187 may be substantially stiffer (e.g., have a greater material stiffness) relative to at least proximal portion 112 to, for example, guide, support, and/or assist distal tip 110 in the penetration of tissue wall 108.

Distal tip 118 may be configured to penetrate tissue wall 108 based on a generally small diameter and/or other dimension determining a contact area between distal tip 118 and tissue wall 108 as distal tip contacts first tissue surface 123 and/or penetrates tissue wall 108. For example, distal tip 118 may define a tip dimension DT determining the contact area when distal tip 118 contacts first tissue surface 123 and/or penetrates tissue wall 108. Tip dimension DT may be selected such that a distal force on elongated body 110 causes distal tip 118 to penetrate tissue wall 108. In some examples, tip dimension DT is less than 0.1 inches, in other examples less than 0.05 inches, and in other dimensions less than 0.02 inches. In some examples, distal tip 118 defines a beveled edge or other form factor configured to reduce a penetration resistance imparted on distal tip 118 when distal tip 118 contacts first tissue surface 123. Elongated body 110 may be configured with a stiffness (e.g., a stiffness along longitudinal axis L) such that a distal force exerted on proximal section 116 causes distal tip 118 to penetrate first tissue surface 123 when distal tip 118 is in contact with first tissue surface 123. In some examples, elongated body 110 defines a proximal end and a length LE from the distal end to the proximal end, and a ratio of the length LE to the tip dimension DT (e.g., the ratio LE/DT) is at least 1000, in some examples at least 1500, and in some examples at least 2000.

FIG. 4 illustrates guide wire system 100 having penetrated tissue wall 108 and support portion 114 having expanded radially outward to define an expanded dimension D2. Expanded dimension D2 is greater than initial dimension D1 defined when support portion 114 (e.g., expansion members 126, 140, 144, 148) is in a relaxed, substantially zero-stress condition. In examples, expanded dimension D2 and initial dimension D1 are perpendicular to the longitudinal axis L defined by elongated body 110. Guide wire system 100 (e.g., elongated body 110) may be configured such that expanded dimension D2 is greater than a dimension of tissue wall puncture 158 generated by distal tip 118. In examples, guide wire system 100 is configured to define expanded dimension D2 such that a proximal force exerted on elongated body 110 causes the expanded support portion 114 to contact and exert a proximal force against second tissue surface 124 rather than translate proximally through tissue wall puncture 158. Inner sheath 186 (FIG. 5A) may be configured to be proximally withdrawn (e.g., by a clinician) relative to elongated body 110 once distal tip 118 has penetrated tissue wall 108 and/or support portion 114 has expanded to define expanded dimension D2.

As discussed, support portion 114 is configured such that a proximal force exerted on distal portion 116 causes distal portion 116 to displace toward proximal portion 112. The displacement may substantially place expansion members 126, 140, 144, 148 in compression, causing expansion members 126, 140, 144, 148 to buckle in a direction away from inner lumen. In examples, an expansion member such as expansion member 140 includes a proximal member end 160 attached to proximal portion 112 and a distal member end 162 opposite the proximal member and attached to distal portion 116. Expansion member 140 may be configured such that a member body 164 defined between proximal member end 160 and distal member end 162 buckles in a direction away from inner lumen 130 when distal member end 162 displaces toward proximal member end 160. In examples, when support portion 114 includes a plurality of expansion members such as expansion member 126, expansion member 140, expansion member 144, and/or expansion member 148, a first expansion member is configured to buckle outwards in a first radial direction from longitudinal axis L and a second expansion member is configured to buckle outwards in a second radial direction from longitudinal axis L different than the first radial direction. Support section 114 may be configured such that the buckled expansion members 126, 140, 144, 148 act to spread a proximal force exerted on elongated body 110 over a substantially circumferential area around tissue wall puncture 158 created by distal tip 118.

Figure 7:
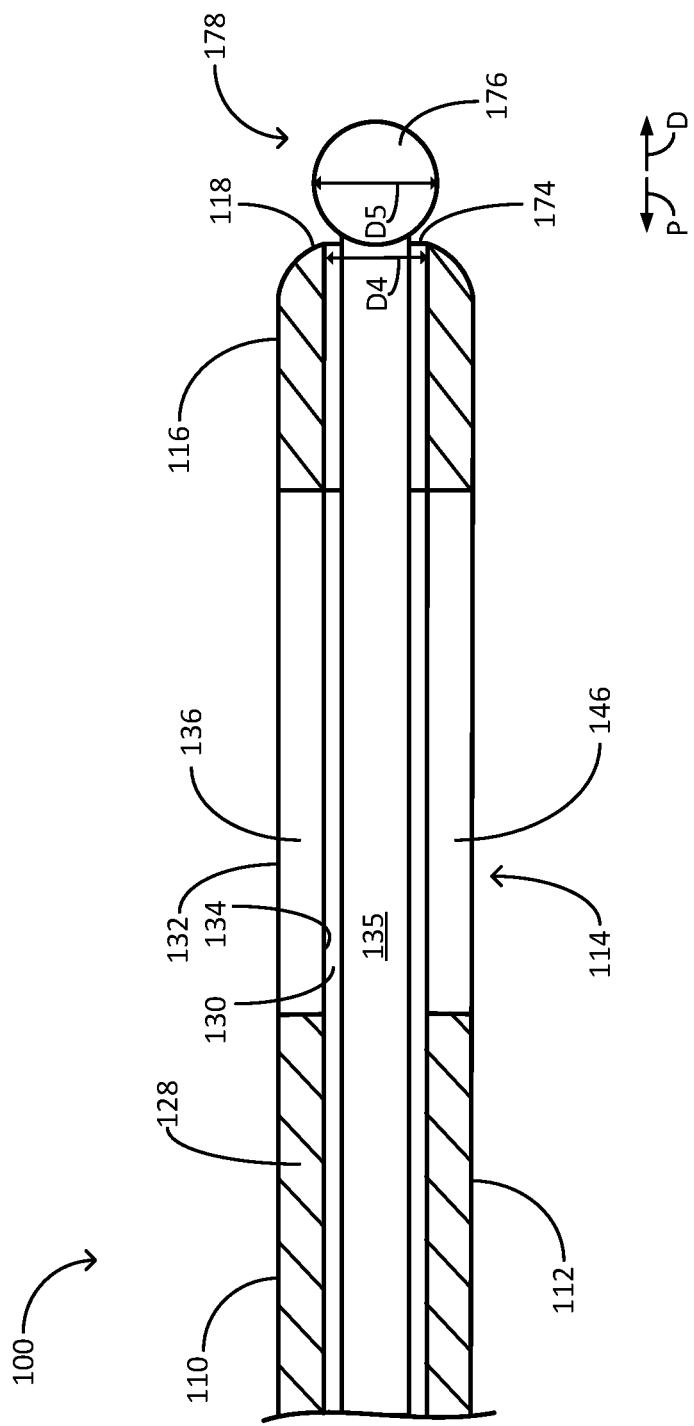
FIG. 7 is a cross-sectional view illustrating an example pull wire within an inner lumen.

Pull wire 135 is configured to exert the proximal force on distal portion 116 to place expansion members 126, 140, 144, 148 in compression to cause support portion 114 to define expanded dimension D2. Pull wire 135 may be configured in any manner sufficient to cause pull wire 135 to exert a proximal force on distal portion 116 when a proximal force is exerted on pull wire 135. In examples, a distal section 166 of pull wire 135 ("pull wire distal section 166") is configured to transfer at least some portion of a proximal force exerted on a proximal section 168 of pull wire 135 ("pull wire proximal section 168") to distal portion 116. In some examples, pull wire distal section 166 is attached to distal portion 116 to transfer the proximal force to distal portion 116. In some examples, pull wire distal section 166 is attached to one or more of expansion members 126, 140, 144, 148, another portion of support portion 114, or some other portion of elongated body 110 to transfer the proximal force to distal portion 116. In some examples, pull wire 135 includes a bearing structure 176 at a distal end 178 of pull wire 135 (FIG. 7) to transfer the proximal force to distal portion 116. Pull wire proximal section 168 may be configured to extend outside a patient, such that a clinician may exert the proximal force on pull wire proximal section 168 to cause the expansion of support portion 114.

Pull wire 135 may be configured to slidably translate within inner lumen 130 to exert the proximal force on distal portion 116. Elongated body 110 may further define inner lumen 130 to extend from support portion 114 through some portion of or substantially all of proximal portion 112. In examples, elongated body 110 defines an opening to inner lumen 130 substantially at a proximal end (not shown) of elongated body 110, and a free end (not shown) of pull wire 135 extends through the proximal opening. Elongated body 110 may be configured such that the proximal opening allows a clinician to exert a proximal force on pull wire 135 from outside a patient when elongated body 110 (e.g., distal tip 118) has penetrated tissue wall 108 within the patient.

In examples, elongated body 110 is configured such that distal tip 118, distal portion 116 and support portion 114 substantially avoid interference (e.g., contact) with structures of second chamber 156 (e.g., RA, LA, RV, or LV of heart 106) when elongated body 110 penetrates tissue wall 108 to position distal tip 118, distal portion 116 and support portion 114 within second chamber 156. In examples, elongated body 110 is configured to extend into second chamber 156 over a distance parallel to longitudinal axis L less than 4.0 centimeters, in some examples less than 2.0 centimeters, when elongated body 110 positions distal tip 118, distal portion 116 and support portion 114 within second chamber 156. Elongated body 110 may be configured such that support portion 114 substantially avoids interference (e.g., contact) with structures of second chamber 156 when support portion 114 expands to define the expanded dimension D2 within second chamber 156. In examples, the expanded dimension D2 is less than 4.0 centimeters, in some examples less than 2.0 centimeters.

As illustrated in FIG. 4, proximal portion 112 may be configured to guide medical device 102 (e.g., lead 122) to target area 104 on first tissue surface 123. Expanded support portion 114 (e.g., the buckled expansion members 126, 140, 144, 146) may be configured to substantially provide support to tissue wall 108 to provide counter-traction to tissue wall 108 when lead 122 exerts a distal force on tissue wall 108. For example, lead 122 may include a fixation device 170 configured to anchor into and/or otherwise penetrate first tissue surface 123 to substantially secure lead 122 to tissue wall 108. Lead 122 may be configured such that a distal force on lead 122 (e.g., imparted by a clinician) causes fixation device 170 to penetrate first tissue surface 123. Lead 122 may transfer some portion of this distal force to tissue wall 108 as fixation device 170 penetrates tissue wall 108 (e.g., first tissue surface 123). Expanded support portion 114 may be configured such that a proximal force on elongated body 110 (e.g., exerted by the clinician) causes support portion 114 to exert a proximal force on second tissue surface 124 as lead 122 transfers the distal force to first tissue surface 123 during penetration, such that the expanded support portion 114 provides a measure of counter-traction and support to tissue wall 108 against the distal force on lead 122. The counter-traction may provide stability to tissue wall 108 or otherwise assist the clinician as the clinician exerts the distal force on lead 122 to cause fixation device 170 to penetrate tissue wall 108.

As discussed, expansion members 126, 140, 144, 148 may be resiliently biased to displace toward inner lumen 130 when the proximal force exerted by pull wire 135 decreases and/or ceases. For example, expansion members 126, 140, 144, 148 may be resiliently biased to displace toward inner lumen 130 when a compressive force on expansion members 126, 140, 144, 148 exerted by distal portion 116 decreases and/or ceases. In some examples, expansion members 126, 140, 144, 148 are configured to define the initial dimension D1 (FIG. 3) when expansion members 126, 140, 144, 148 are in a substantially zero-stress condition. As used herein, when expansion members 126, 140, 144, 148 are in a zero-stress condition, this may mean that any stresses on expansion members 126, 140, 144, 148 arise from properties or phenomena internal to expansion members 126, 140, 144, 148, such as mass, internal temperature, residual stresses, and the like. Hence, expansion members 126, 140, 144, 148 may be resiliently biased such that when a clinician decreases and/or ceases exerting a proximal force on pull wire 135, expansion members 126, 140, 144, 148 substantially collapse from the expanded (e.g., buckled) condition defining the expanded dimension D2 to define the initial dimension D1, such that support portion 114, distal portion 116, and distal tip 118 may be withdrawn back through tissue wall 108 once lead 122 is positioned, or for other reasons. Additionally, expansion members 126, 140, 144, 148 may be configured such that exerting a distal force (e.g., in the distal direction D) on pull wire 135 while maintaining elongated body 110 substantially stationary with respect to tissue wall 108 causes and/or assists with expansion members 126, 140, 144, 148 collapsing to define the initial dimension D1.

In examples, lead 122 defines a lead lumen 172. Elongated body 110 is configured such that at least some portion of proximal section 116 is configured to pass though lead lumen 172. Elongated body 110 may be configured to allow lead lumen 172 to translate over the portion of proximal section 116, such that, for example, elongated body 110 may guide lead 122 to target area 104. Elongated body 110 may be configured such that support portion 114 is configured to pass through lead lumen 172 when expansion members 126, 140, 144, 148 define the initial dimension D1 (e.g., in the relaxed configuration). Elongated body 110 may be configured such that the expanded dimension D2 prevents support portion 114 from passing through lead lumen 172 when expansion members 126, 140, 144, 148 define the expanded dimension D2 (e.g., when in the compressed, buckled condition). In examples, lead lumen 172 defines a cross-sectional lumen dimension D3 (e.g., a diameter). The initial dimension D1 may be less than the cross-sectional lumen dimension D3 and the expanded dimension D2 may be greater than the cross-sectional lumen dimension D3.

FIG. 6A and FIG. 6B illustrate and end view of guide wire system 100 including a plurality of expansion members 126, 140, 144, 148 configured to spread a proximal force (e.g., a counter-traction force) over a substantially circumferential area around tissue wall puncture 158 (FIGS. 2-4) created by distal tip 118. FIG. 6A illustrates guide wire system 100 in the absence of a proximal force exerted by pull wire 135 on distal portion 116, such that expansion members 126, 140, 144, 148 are the relaxed condition defining initial dimension D1. FIG. 6A illustrates guide wire system 100 in the absence of a proximal force exerted by pull wire 135 on distal portion 116, such that expansion members 126, 140, 144, 148 are the relaxed condition defining initial dimension D1. In FIGS. 6A and 6B, the proximal direction P is perpendicular to and into the page and the distal direction D is perpendicular to and out of the page.

Expansion members 126, 140, 144, 148 are configured to buckle outwards and cause support portion 114 to expand from the initial dimension D1 to the expanded dimension D2 when a proximal force exerted by pull wire 135 places expansion members 126, 140, 144, 148 in compression. In examples, each of expansion members 126, 140, 144, 148 is configured to buckle outwards in a substantially different radial direction from longitudinal axis L, such that the expanded support portion 114 forms a petal-type shape to spread the proximal force exerted by pull wire 135 over a larger area of second tissue surface 124 (FIGS. 1-4). For example, expansion member 126 may be configured to buckle outward in the first radial direction R1 when placed in compression. Expansion member 140 may be configured to buckle outward in the second radial direction R2 when placed in compression. Expansion member 144 may be configured to buckle outward in the third radial direction R3 when placed in compression, and expansion member 148 may be configured to buckle outward in the fourth radial direction R4 when placed in compression. Each of radial directions R1, R2, R3, R4 may define a different radial direction than at least one other of R1, R2, R3, R4.

Expansion members 126, 140, 144, 148 may be configured to be spaced apart from each other when support portion 114 is in the expanded condition. For example, FIG. 6B illustrates expansion member 126 and expansion member 140 spaced apart from each other by a distance 51. Distance 51 may be expressed as a linear distance over a line oriented perpendicular to longitudinal axis L, and may be between any portion of expansion member 126 and any portion of expansion member 140. In examples, distance 51 may be expressed as an angle having a vertex on longitudinal axis L. For example, distance 51 may be expressed as an angle in the range of 30 to 180 degrees. The illustrated number and arrangement of expansion members 126, 140, 144, 148 is one non-limiting example, and guide wire system 100 may, in other examples, include a different number of expansion members and/or a different positions of one or more individual expansion members. In an example, guide wire system 100 includes a plurality of expansion members such as expansion members 126, 140, 144, 148 distributed substantially equally around longitudinal axis L on a circumference of elongated body 110. First slit 136 may be configured to expand (e.g., increase its width) when expansion member 126 buckles in the first radial direction R1 and expansion member 140 buckles in the second radial direction R2.

Expansion members 126, 140, 144, 148 may be resiliently biased to displace toward inner lumen 130 when the proximal force exerted by pull wire 135 decreases and/or ceases. Thus, guide wire system 100 is configured such that a proximal force exerted on pull wire 135 causes support portion 114 to transition from the relaxed condition of FIG. 6A defining initial dimension D1 to the expanded condition of FIG. 6B defining expanded dimension D2. Guide wire system 100 may be configured such that decreasing and/or ceasing the proximal force on pull wire 135 causes support portion 114 to transition from the expanded condition of FIG. 6B defining expanded dimension D2 to the relaxed condition of FIG. 6A defining initial dimension D1. For example, guide wire system 100 may be configured such decreasing and/or ceasing the proximal force on pull wire 135 as support portion 114 is withdrawn proximally through a tissue wall puncture formed by distal tip 118 causes support portion 114 to transition from the expanded condition of FIG. 6B to the relaxed condition of FIG. 6A.

Hence, guide wire system 100 may be configured to establish and/or substantially maintain the initial dimension D1 as distal tip 118, distal portion 116, and support portion 114 penetrate tissue wall 108 in the vicinity of target area 104. Guide wire system 100 may be configured to establish the expanded dimension D2 to maintain elongated body 110 substantially secured to tissue wall 108 as lead 122 is distally translated over elongated body 110 enroute to target area 104. Guide wire system 100 may be configured to provide a proximal force on tissue wall 108 when lead 122 exerts a distal force on tissue wall 108 (e.g., when fixation device 170 is caused to penetrate tissue wall 108). Guide wire system 100 may be configured to substantially, re-establish the initial dimension D1, such that distal tip 118, distal portion 116, and support portion 114 may be withdrawn proximally through tissue wall puncture 158 and lead lumen 172 when lead 122 is secured to tissue wall 108.

Pull wire 135 may have any configuration sufficient to exert a proximal force (e.g., in the proximal direction P) on distal portion 116. In some examples, and referring to FIG. 7, elongated body 110 may define inner lumen 130 to extend through distal portion 116 and define a distal opening 174 to inner lumen 130 in distal tip 118. Elongated body 110 is depicted in cross-section in FIG. 7 with a cutting plane parallel to the page. Pull wire 135 may be configured to extend through inner lumen 130 and distal opening 174. In examples, pull wire 135 includes a bearing structure 176 at a distal end 178 of pull wire 135 ("pull wire distal end 178") configured to extend distal to distal opening 174. In examples, bearing structure 176 is configured to exert a proximal force on distal portion 116 (e.g., around some portion of a periphery of distal opening 174) when a proximal force is exerted on pull wire 135. In examples, distal opening 174 and/or inner lumen 130 defines a lumen dimension D4 (e.g., a diameter) configured to allow pull wire 135 to translate within inner lumen 130, and bearing structure 176 defines a structure dimension D5 (e.g., a diameter) configured to cause bearing structure 176 to contact distal portion 116 and exert a proximal force on distal portion 116 when pull wire 135 translates proximally within inner lumen 130. Bearing structure 176 and/or distal opening 174 may define any shape. In examples, bearing structure 176 defines a substantially spherical shape having a diameter defining the structure dimension D5. In examples, distal opening 174 is a substantially circular opening having a diameter defining the lumen dimension D4.

Pull wire 135 may be configured to penetrate tissue wall 108 (FIGS. 1-4) to, for example, assist with the penetration of distal tip 118 through tissue wall 108. Pull wire 135 may be configured to extend distal to distal tip 118 (e.g., translate distally relative to distal tip 118), such that pull wire distal end 178 may pass from first tissue surface 123 to second tissue surface 124 as distal tip 118 remains adjacent first tissue surface 123. In examples, pull wire distal end 178 is configured to penetrate tissue wall 108 (FIGS. 1-4) when pull wire distal end 178 contacts tissue wall 108 and a distal force (e.g., in the direction D) is exerted on pull wire distal end 178. Penetration of tissue wall 108 with pull wire distal end 178 prior to distal tip 118 may assist with and/or ease the subsequent penetration of tissue wall 108 by distal tip 118.

Figure 8:
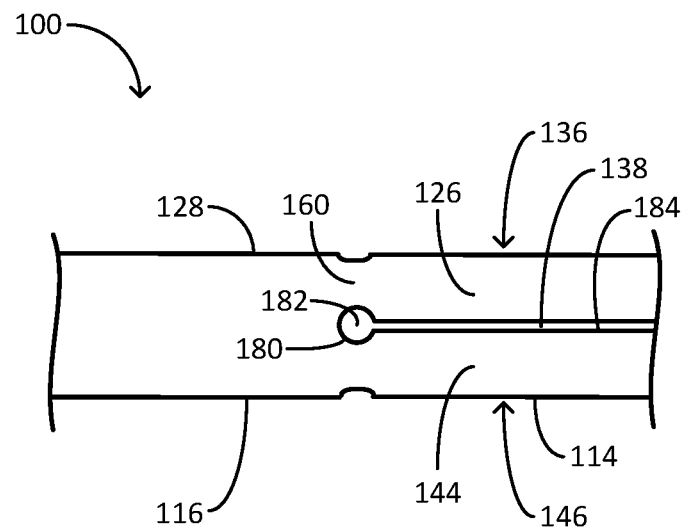
FIG. 8 is a conceptual diagram illustrating an example structure of an elongated body.

FIG. 8 illustrates a guide wire system 100 including a feature 180 configured to reduce a mechanical stress experienced by expansion member 126 when expansion member 126 expands radially outward (e.g., when expansion members 126, 140, 144, 148 define the expanded dimension D2). Elongated body 110 may define feature 180. In examples, feature 180 defines a first volume and/or first area (e.g., relief notch area 182) contiguous with a second volume and/or second area (e.g., slit area 184) defined within second slit 138. Feature 180 may be configured to reduce and/or eliminate a stress concentration on expansion member 126 that might occur in the absence of feature 180. In examples, feature 180 is configured to define a curved material boundary at an end (e.g., proximal member end 160) of an expansion member 126 to limit and/or substantially avoid corners and other structures which may generate stress concentrations when expansion member 126 buckles to define the expanded dimension D2 (FIG. 4). In examples, elongated body 110 defines a first width and a second width across second slit 138, where the first width is parallel to the second width, and where the first width is less than the second width. In some examples, feature 180 is a substantially circular feature extending through wall 128 to inner lumen 130 (FIGS. 2-5B).

Figure 9:
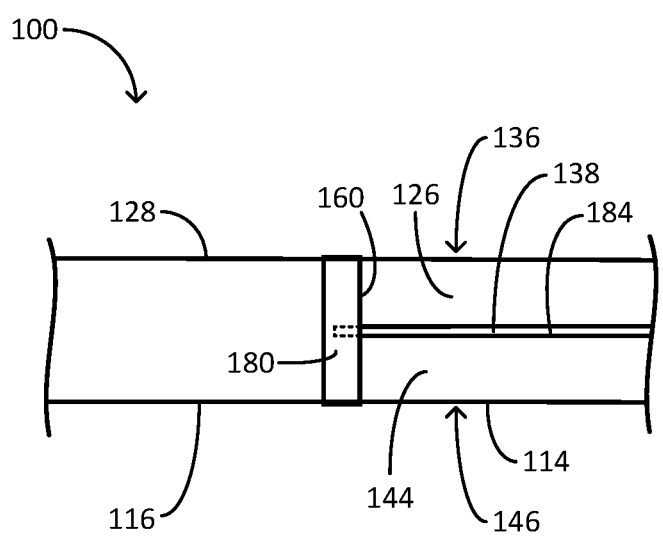
FIG. 9 is a conceptual diagram illustrating another example structure of an elongated body.

In some examples, as illustrated in FIG. 9, elongated body 110 defines feature 180 as an additional amount of material configured to reduce a mechanical stress experienced by expansion member 126 when expansion member 126 expands radially outward. Feature 180 may be, for example, a band and/or strip of material around at least some portion of a periphery of elongated body 110. The band and/or strip may comprise a portion of wall 128. In some examples, the band and/or strip is an integral feature defined by a material comprising wall 128. In some examples, the band and/or strip comprises a component fixably attached to elongated body 110 by heat shrinking, adhesive, or some other method. In examples, elongated body 110 defines a first thickness and a second thickness of wall 128, where the first thickness is parallel to the second thickness, and where the first thickness is less than the second thickness. In examples, the first thickness and the second thickness define a displacement between exterior surface 132 and interior surface 134 (FIGS. 2-5B).

Elongated body 110 may be a flexible lead configured to allow positioning of distal portion 116 and/or distal tip 118 relative to portions of proximal section 112 in a variety of relative orientations. In examples, proximal portion 112 is configured to flex to define a primary curvature and a secondary curvature, with the primary curvature defining a curvature in a primary plane (e.g., a primary Euclidean plane) and the secondary curvature defining a curvature in a secondary plane (e.g., a secondary Euclidean plane). The primary plane and the secondary plane may define an angle between the primary plane and the secondary plane when proximal portion 112 defines primary curvature and secondary curvature, such that the primary curvature and secondary curvature are out-of-plane with one another. Pull wire 135 may be configured to exert the proximal force on distal portion 116 to cause expansion of support portion 114 when proximal section 112 defines the primary curvature and the secondary curvature. In examples, elongated body 110 defines inner lumen 130 to extend through some portion of proximal portion 112, and pull wire 135 extends through inner lumen 130 within a section of proximal portion 112 defining the primary curvature and the secondary curvature.

Guide wire system 100 may include any material. In examples, guide wire system 100 includes one or more bio-compatible materials such as Nitonol. Elongated body 110 may define proximal portion 112, support portion 114, distal portion 116, and/or distal tip 118 in any manner. In examples, two or more of proximal portion 112, support portion 114, distal portion 116, and/or distal tip 118 may be defined as portions of a single piece of a common material. In some examples, proximal portion 112, support portion 114, distal portion 116, and distal tip 118 are all defined as portions of a single piece of a common material. In some examples, elongated body 110 is tubular member defining inner lumen 130 from proximal portion 112 to at least distal portion 116. Slits 136, 138, 142, 146 may be formed as cut-outs (e.g., by laser cutting) through wall 128 of the tubular member. In some examples, proximal portion 112, support portion 114, distal portion 116, and/or distal tip 118 are separately fabricated elements attached to an adjacent portion by welding, soldering, an adhesive, or some other fixation method.

Figure 10:
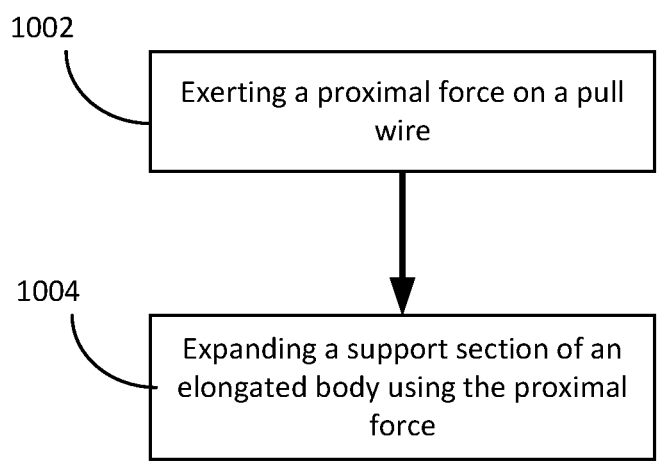
FIG. 10 illustrates an example technique for positioning a guide wire system within a heart.

A technique for securing a guide wire system 100 within an atrium of a heart is illustrated in FIG. 10. Although the technique is described mainly with reference to guide wire system 100 of FIGS. 1-9, the technique may be applied to other medical systems in other examples.

The technique includes exerting a proximal force on a pull wire 135 of guide wire system 100 (1002). In examples, the technique includes navigating elongated body 110 to tissue wall 108 of heart 106. The technique may include causing distal tip 118 to penetrate tissue wall 108 prior to exerting the proximal force. Tissue wall 108 may separate a first chamber 154 and a second chamber 156 of heart 106. In examples, the technique includes positioning elongated body 110 such that support portion 114, distal portion 116, and distal tip 118 are located within second chamber 156 as proximal portion 112 is positioned within first chamber 154.

The technique may include causing distal tip 118 to penetrate tissue wall 108 by exerting a proximal force on elongated body 110. Elongated body 110 may include wall 128 defining inner lumen 130 extending at least through support portion 114. The technique may include positioning expansion members 126, 140, 144, 148 within second chamber 156 when support portion 114 positions within second chamber 156. Expansion members 126, 140, 144, 148 may be defined by slits 136, 138, 142, 146 extending through wall 128 to inner lumen 130. In examples, inner sheath 186 (e.g., sheath lumen 188) supports and/or guides elongated body 110 as distal tip penetrates tissue wall 108.

The technique may include causing distal tip 118 to penetrate tissue wall 108 while support portion 114 (e.g., expansion members 126, 140, 144, 148) define the initial dimension D1. Expansion members 126, 140, 144, 148 may define the initial dimension D1 when expansion members 126, 140, 144, 148 are in a relaxed, substantially zero-stress condition. In examples, a resilient biasing of expansion members 126, 140, 144, 148 causes support portion 114 to define the initial dimension D1. In examples, the technique includes exerting a distal force on elongated body 110 to cause distal tip 118 to penetrate first tissue surface 123 of tissue wall 108 and exit through second tissue surface 124. First tissue surface 123 may be a tissue surface in a first chamber 154 (e.g., the RA, LA, RV, or LV) of heart 106. Second tissue surface 124 may be a tissue surface in a second chamber 156 (e.g., the RA, LA, RV, or LV) of heart 106.

In examples, distal tip 118 causes a tissue wall puncture 158 through tissue wall 108 when distal tip 118 penetrates tissue wall 108. In examples, distal portion 116 and support portion 114 pass through tissue wall puncture 158 to position within second chamber 156. The technique may include establishing a contact area between distal tip 118 and tissue wall 108 as distal tip contacts first tissue surface 123 and/or penetrates tissue wall 108. A tip dimension DT may determine the contact area. In examples, a beveled edge or other form factor reduces a penetration resistance when distal tip 118 penetrates tissue wall 108.

The technique includes radially expanding expansion members 126, 140, 144, 148 using the proximal force on pull wire 135 (1004). In examples, pull wire 135 exerts a proximal force on distal portion 116 when the proximal force is exerted on pull wire 135. Distal portion 116 may exert a compressive force on expansion members 126, 140, 144, 148 when pull wire 135 exerts the proximal force on distal portion 116. In examples, the proximal force exerted on pull wire 135 places expansion members 126, 140, 144, 148 in compression. Expansion members 126, 140, 144, 148 may buckle outwards in a radial direction away from longitudinal axis L when expansion members 126, 140, 144, 148 are placed in compression.

The technique may include causing expansion members 126, 140, 144, 148 to expand radially outward to define the expanded dimension D2 using the proximal force on pull wire 135. In examples, the technique includes causing expansion members 126, 140, 144, 148 to expand radially outward when support portion 114 is positioned in second chamber 156. The proximal force exerted on pull wire 135 may exert a proximal force on distal portion 116 causing distal portion 116 to displace toward proximal portion 112 to place expansion members 126, 140, 144, 148 in compression. The compression may cause member body 164 between proximal member end 160 and distal member end 162 of expansion member 140 to buckle in a direction away from inner lumen 130. In examples, the compression causes expansion member 126 to buckle outward in the first radial direction R1, expansion member 140 to buckle outward in the second radial direction R2, expansion member 144 to buckle outward in the third radial direction R3, and/or expansion member 148 to buckle outward in the fourth radial direction R4.

The technique may include using proximal portion 112 to guide a medical device 102 (e.g., lead 122) to target area 104 on first tissue surface 123 when support portion 114 is in the expanded condition. Expanded support portion 114 may provide support to tissue wall 108 to provide counter-traction to tissue wall 108 as lead 122 exerts a distal force on tissue wall 108. In examples, expanded support portion 114 exerts a proximal force on second tissue surface 124 when medical device 102 and/or lead 122 exerts a distal force on lead 122. In examples, expanded support portion exerts a proximal force on second tissue surface 124 when fixation device 170 penetrate first tissue surface 123. The technique may include exerting a distal force on medical device 102 and/or lead 122 while exerting a proximal force on elongated body 110, such that the expanded support portion 114 provides a measure of counter-traction and support to tissue wall 108 against the distal force exerted by medical device 102 and/or lead 122.

The technique may include decreasing and/or ceasing to exert the proximal force on pull wire 135 to cause support portion 114 to re-establish the initial dimension D1. In examples, the technique includes causing support portion 114 (e.g., expansion members 126, 140, 144, 148) to define the initial dimension D1 by withdrawing support portion 114 proximally through tissue wall 108 (e.g., through a tissue wall puncture substantially formed by distal tip 118). The resilient biasing of expansion members 126, 140, 144, 148 may cause expansion members 126, 140, 144, 148 to displace toward inner lumen 130 when the proximal force is decreased and/or ceased. The technique may include withdrawing support portion 114, distal portion 116, and distal tip 118 proximally back through tissue wall 108 when support portion 114 re-establishes the initial dimension D1. In examples, the technique includes withdrawing support portion 114, distal portion 116, and distal tip 118 proximally back through a lumen of medical device 102 and/or lead 122 (e.g., lead lumen 172) when support portion 114 re-establishes the initial dimension D1.

The disclosure includes the following examples.

Example 1: A guide wire system comprising: an elongated body defining a proximal portion, a support portion, a distal portion, and a distal tip at a distal end of the elongated body; wherein the elongated body includes a body wall defining an inner lumen within at least the support portion, wherein the elongated body defines at least two slits extending through the wall in the support portion and the elongated body defines an expansion member between the two slits, and wherein the distal tip is configured to penetrate a tissue wall; and a pull wire configured to exert a proximal force on the distal portion of the elongated body when the proximal force is exerted on the pull wire, wherein the expansion member is configured to expand radially outward from the inner lumen when the proximal force is exerted on the distal portion.

Example 2: The guide wire system of example 1, wherein the elongated body is configured to cause the distal tip to pass through the tissue wall such that the support portion is between the distal tip and the tissue wall; and wherein the expansion member is configured to expand radially outward such that the expansion member exerts a proximal force against the tissue wall when a proximal force is exerted on the elongated body.

Example 3: The guide wire system of example 2, wherein the tissue wall is a septum separating a first chamber and a second chamber of a heart.

Example 4: The guide wire system of any of examples 1-3, wherein the elongated body defines a longitudinal axis extending within the inner lumen at least through the support portion, and wherein the two slits are substantially parallel to the longitudinal axis.

Example 5: The guide wire system of any of examples 1-4, wherein the elongated body defines a plurality of expansion members in the support portion, wherein each expansion member is between a first longitudinal slit and a second longitudinal slit.

Example 6: The guide wire system of example 5, wherein each expansion member in the plurality is configured to expand radially outward from the inner lumen when the proximal force is exerted on the distal portion.

Example 7: The guide wire system of any of examples 1-6, wherein the expansion member is resiliently biased to displace toward the inner lumen when the proximal force exerted by the pull wire decreases.

Example 8: The guide wire system of any of examples 1-7, wherein: the elongated body defines a longitudinal axis extending within the inner lumen at least through the support portion, the expansion member is configured to expand radially outward from an initial dimension defined from the longitudinal axis to an expanded dimension defined from the longitudinal axis when the proximal force is exerted on the pull wire, and the expansion member is resiliently biased to substantially establish the initial dimension when the proximal force on the pull wire is removed.

Example 9: The guide wire system of any of examples 1-8, wherein the body wall further defines the inner lumen within the proximal portion, and wherein the pull wire extends through the inner lumen within the proximal portion.

Example 10: The guide wire system of any of examples 1-9, wherein a distal portion of the pull wire is secured to the distal portion of the elongated body.

Example 11: The guide wire system of any of examples 1-10, wherein a distal portion of the pull wire is secured to the inner lumen.

Example 12: The guide wire system of any of examples 1-11, wherein the expansion member has a first end attached to the proximal section and a second end attached to the distal portion, and wherein the expansion member is configured such that the second end displaces proximally toward the first end when the expansion member expands radially outward from the inner lumen.

Example 13: The guide wire system of any of examples 1-12, wherein a portion of the expansion member is configured to experience a mechanical stress when the expansion member expands radially outward from the inner lumen, and wherein the elongated body includes a feature configured to reduce the mechanical stress experienced by the expansion member.

Example 14: The guide wire system of any of examples 1-13, wherein the elongated body defines a first width across a longitudinal slit and defines a second width across the longitudinal slit, wherein the first width is parallel to the second width, and wherein the first width is less than the second width.

Example 15: The guide wire system of example 14, wherein: a portion of the elongated body defining the first width and the second width defines a portion of the expansion member, the portion of the expansion member is configured to experience a mechanical stress when the expansion member expands radially outward from the inner lumen, and the first width and the second width are configured to reduce the mechanical stress experienced by the portion of the expansion member.

Example 16: The guide wire system of any of examples 1-15, wherein the elongated body defines a first thickness of the expansion member and a second thickness of the expansion member, wherein the first thickness is parallel to the second thickness, and wherein the first thickness is less than the second thickness.

Example 17: The guide wire system of example 16, wherein: a portion of the elongated body defining the first thickness and the second thickness defines a portion of the expansion member, the portion of the expansion member is configured to experience a mechanical stress when the expansion member expands radially outward from the inner lumen, and the first thickness and the second thickness are configured to reduce the mechanical stress experienced by the portion of the expansion member.

Example 18: The guide wire system of any of examples 1-17, wherein the proximal portion of the elongated body is configured to pass through a lead lumen defined by a lead, and wherein the expansion member is configured to expand radially outward to prevent the support portion, the distal portion, and the distal tip from passing through the lead lumen.

Example 19: The guide wire system of example 18, wherein the expansion member is resiliently biased to displace toward the inner lumen when the proximal force exerted by the pull wire decreases, and wherein the support portion, the distal portion, and the distal tip are configured to pass through the lead lumen when the expansion member displaces toward the inner lumen.

Example 20: The guide wire system of example 18 or example 19, further comprising the lead.

Example 21: A guide wire system comprising: an elongated body defining a proximal portion, a support portion, a distal portion, and a distal tip at a distal end; wherein the elongated body includes a body wall defining an inner lumen within the support portion, wherein the elongated body defines a longitudinal axis extending within the inner lumen at least through the support portion, wherein the elongated body defines at least two slits substantially parallel to the longitudinal axis and extending through the wall in the support portion and the elongated body defines an expansion member between the two slits, and wherein the distal tip is configured to penetrate a tissue wall; and a pull wire configured to exert a proximal force on the distal portion of the elongated body when the proximal force is exerted on the pull wire, wherein the expansion member is configured to expand radially outward from the inner lumen when the proximal force is exerted on the distal portion, and wherein the expansion member is resiliently biased to displace toward the inner lumen when the proximal force exerted by the pull wire decreases.

Example 22: The guide wire system of example 21, wherein the tissue wall is a septum separating a first chamber and a second chamber of a heart, wherein the elongated body is configured to cause the distal tip to pass through the septum such that the support portion is between the distal tip and the septum, and wherein the expansion member is configured to expand radially outward such that the expansion member exerts a proximal force against the tissue wall when a proximal force is exerted on the elongated body.

Example 23: The guide wire system of example 21 or example 22, wherein the elongated body defines a plurality of expansion members in the support portion, wherein each expansion member is between a first longitudinal slit and a second longitudinal slit.

Example 24: The guide wire system of any of examples 21-23, wherein each expansion member in the plurality is configured to expand radially outward from the inner lumen when the proximal force is exerted on the distal portion.

Example 25: The guide wire system of any of examples 21-24, wherein the expansion member is resiliently biased to displace toward the inner lumen when the proximal force exerted by the pull wire decreases.

Example 26: The guide wire system any of examples 21-25, wherein: the expansion member is configured to expand radially outward from an initial dimension defined from the longitudinal axis to an expanded dimension defined from the longitudinal axis when the proximal force is exerted on the pull wire, and the expansion member is resiliently biased to substantially establish the initial dimension when the proximal force on the pull wire is removed.

Example 27: The guide wire system of any of examples 21-26, wherein the body wall further defines the inner lumen within the proximal portion, and wherein the pull wire extends through the inner lumen in the proximal portion.

Example 28: The guide wire system of any of examples 21-27, wherein a distal portion of the pull wire is secured to the distal portion of the elongated body.

Example 29: The guide wire system of any of examples 21-28, wherein a distal portion of the pull wire is secured to the inner lumen.

Example 30: The guide wire system of any of examples 21-29, wherein the expansion member has a first end attached to the proximal section and a second end attached to the distal portion, and wherein the expansion member is configured such that the second end displaces proximally toward the first end when the expansion member expands radially outward from the inner lumen.

Example 31: The guide wire system of any of examples 21-30, wherein a portion of the expansion member is configured experience a mechanical stress when the expansion member expands radially outward from the inner lumen, and wherein the elongated body includes a feature configured to reduce the mechanical stress experienced by the expansion member.

Example 32: The guide wire system of any of examples 21-31, wherein the elongated body defines a first width across a longitudinal slit and defines a second width across the longitudinal slit, wherein the first width is parallel to the second width, and wherein the first width is less than the second width.

Example 33: The guide wire system of example 32, wherein: a portion of the elongated body defining the first width and the second width defines a portion of the expansion member, the portion of the expansion member is configured to experience a mechanical stress when the expansion member expands radially outward from the inner lumen, and the first width and the second width are configured to reduce the mechanical stress experienced by the portion of the expansion member.

Example 34: The guide wire system of any of examples 21-33, wherein the elongated body defines a first thickness of the expansion member and a second thickness of the expansion member, wherein the first thickness is parallel to the second thickness, and wherein the first thickness is less than the second thickness.

Example 35: The guide wire system of example 34, wherein: a portion of the elongated body defining the first thickness and the second thickness defines a portion of the expansion member, the portion of the expansion member is configured to experience a mechanical stress when the expansion member expands radially outward from the inner lumen, and the first thickness and the second thickness are configured to reduce the mechanical stress experienced by the portion of the expansion member.

Example 36: The guide wire system of any of examples 21-35, further comprising a lead defining a lead lumen, wherein the proximal portion of the elongated body is configured to pass through a lead lumen defined by a lead, and wherein the expansion member is configured to expand radially outward to prevent the support portion, the distal portion, and the distal tip from passing through the lead lumen.

Example 37: The guide wire system of example 36, wherein the support portion, the distal portion, and the distal tip are configured to pass through the lead lumen when the expansion member displaces toward the inner lumen.

Example 38: A method, comprising: exerting, using a pull wire, a force in a proximal direction on a distal portion of an elongated body comprising a proximal portion, and support portion, the distal portion, and a distal tip configured to penetrate a tissue wall at a distal end; and radially expanding, using the force on the distal portion, an expansion member defined between at least two slits extending through a wall of the elongated body, wherein the wall defines an inner lumen within the support portion.

Example 39: The method of example 38, further comprising: translating the elongated body to cause the distal tip to pass through the tissue wall such that the support portion is between the distal tip and the tissue wall; expanding the expansion member of the translated elongated body radially outward; and causing the expansion member to exert a proximal force against the tissue wall by exerting a proximal force on the elongated body.

Example 40: The method of example 38 or example 39, wherein the tissue wall is a septum separating a first chamber and a second chamber of a heart.

Example 41: The method of any of examples 38-40, further comprising causing the expansion member to displace toward the inner lumen by decreasing the proximal force exerted by the pull wire.

Example 42: The method of any of examples 38-41, wherein the expansion section has a first end attached to the proximal section and a second end attached to the distal portion, and further comprising displacing the second end toward the first end when the expansion member expands radially outward from the inner lumen.

Example 43: The method of any of examples 38-42, wherein a portion of the expansion member is configured experience a mechanical stress when the expansion member expands radially outward from the inner lumen, and further comprising reducing the mechanical stress experienced using a feature defined by the elongated body.

Example 44: The method of any of examples 38-43, further comprising: translating a lead over the proximal portion of the elongated body by causing the proximal portion to pass through a lead lumen defined by the lead; and preventing the expansion portion, the distal portion, and the distal tip from passing through the lead lumen using the radially expanded expansion portion.

Example 45: The method of example 44, further comprising: decreasing the proximal force exerted by the pull wire; displacing the radially expanded expansion member toward the inner lumen using the decreased proximal force; and passing the expansion portion having the displaced expansion member, the distal portion, and the distal tip through the lead lumen.

Various examples of the disclosure have been described. Any combination of the described systems, operations, or functions is contemplated. These and other examples are within the scope of the following claims.

What is claimed is:

1. A guide wire system comprising:
   an elongated body defining a proximal portion, a support portion, a distal portion, and a distal tip at a distal end of the elongated body;
   wherein the elongated body includes a body wall defining an inner lumen within at least the support portion,
   wherein the elongated body defines at least two slits extending through the wall in the support portion and the elongated body defines an expansion member between the two slits, and
   wherein the distal tip is configured to penetrate a tissue wall; and
   a pull wire configured to exert a proximal force on the distal portion of the elongated body when the proximal force is exerted on the pull wire, wherein the expansion member is configured to expand radially outward from an initial dimension to an expanded dimension when the proximal force is exerted on the distal portion,
   wherein the distal portion defines a cross-sectional dimension substantially equal to the initial dimension, and
   wherein the expansion member is resiliently biased to displace toward the inner lumen and return to defining the initial dimension when the proximal force exerted by the pull wire decreases.

2. The guide wire system of claim 1,
   wherein the elongated body is configured to cause the distal tip to pass through the tissue wall such that the support portion is between the distal tip and the tissue wall; and
   wherein the expansion member is configured to expand radially outward such that the expansion member exerts a proximal force against the tissue wall when a proximal force is exerted on the elongated body.

3. The guide wire system of claim 1, wherein the elongated body defines a longitudinal axis extending within the inner lumen at least through the support portion, and wherein the two slits are substantially parallel to the longitudinal axis.

4. The guide wire system of claim 1, wherein the elongated body defines a plurality of expansion members in the support portion, wherein each expansion member is between a first longitudinal slit and a second longitudinal slit.

5. The guide wire system of claim 4, wherein each expansion member in the plurality is configured to expand radially outward from the inner lumen when the proximal force is exerted on the distal portion.

6. The guide wire system of claim 1, wherein the expansion member is configured to displace inward toward the inner lumen when the proximal force exerted by the pull wire decreases and a tissue wall exerts a force toward the inner lumen on the expansion member.

7. The guide wire system of claim 1, wherein the body wall further defines the inner lumen within the proximal portion, and wherein the pull wire extends through the inner lumen within the proximal portion.

8. The guide wire system of claim 1, wherein the elongated body defines a distal opening which opens to the inner lumen, wherein the pull wire extends through the distal opening, and wherein the pull wire includes a bearing structure at a distal end of the pull wire, wherein the bearing structure is configured to exert the proximal force on the distal portion when a proximal force is exerted on the pull wire.

9. The guide wire system of claim 1, wherein a distal portion of the pull wire is secured to at least one of the distal portion of the elongated body or the inner lumen.

10. The guide wire system of claim 1, wherein the expansion member has a first end attached to the proximal section and a second end attached to the distal portion, and wherein the expansion member is configured such that the second end displaces proximally toward the first end when the expansion member expands radially outward from the inner lumen.

11. The guide wire system of claim 1, wherein a portion of the expansion member is configured to experience a mechanical stress when the expansion member expands radially outward from the inner lumen, and wherein the elongated body includes a feature configured to reduce the mechanical stress experienced by the expansion member.

12. The guide wire system of claim 1, further comprising a lead defining a lead lumen,
wherein the proximal portion of the elongated body is configured to pass through a lead lumen defined by a lead, and
wherein the expansion member is configured to expand radially outward to prevent the support portion, the distal portion, and the distal tip from passing through the lead lumen.

13. The guide wire system of claim 1, further comprising an inner sheath including a sheath body defining a lumen, wherein the inner sheath includes a fixation element configured to engage tissue, and wherein the elongated body is configured to translate within the lumen.

14. A guide wire system comprising:
an elongated body defining a proximal portion, a support portion, a distal portion, and a distal tip at a distal end,
wherein the elongated body includes a body wall defining an inner lumen at least within the support portion,
wherein the elongated body defines at least two slits extending through the wall in the support portion and the elongated body defines an expansion member between the two slits, and
wherein the distal tip is configured to penetrate a tissue wall;
a pull wire configured to exert a proximal force on the distal portion of the elongated body when the proximal force is exerted on the pull wire, wherein the expansion member is configured to expand radially outward from the inner lumen when the proximal force is exerted on the distal portion; and
an inner sheath including a sheath body defining a lumen, wherein the inner sheath includes a fixation element configured to engage tissue, and wherein the elongated body is configured to translate within the lumen.

15. The guide wire system of claim 14,
wherein the tissue wall is a septum separating a first chamber and a second chamber of a heart,
wherein the elongated body is configured to cause the distal tip to pass through the septum such that the support portion is between the distal tip and the septum, and
wherein the expansion member is configured to expand radially outward such that the expansion member exerts a proximal force against the tissue wall when a proximal force is exerted on the elongated body.

16. The guide wire system of claim 14, wherein the body wall further defines the inner lumen within the proximal portion, and wherein the pull wire extends through the inner lumen in the proximal portion.

17. A method, comprising:
translating an elongated body within a lumen defined by a sheath body of an inner sheath, the inner sheath including a fixation element configured to engage tissue;
exerting, using a pull wire, a force in a proximal direction on a distal portion of an elongated body defining a proximal portion, a support portion, the distal portion, and a distal tip at a distal end of the elongated body, the distal tip configured to penetrate a tissue wall at a distal end; and
radially expanding, using the force on the distal portion, an expansion member of the elongated body, the expansion member defined between at least two slits extending through a body wall of the elongated body in the support portion, wherein the body wall defines an inner lumen within the support portion.

18. The method of claim 17, further comprising:
translating the elongated body to cause the distal tip to pass through the tissue wall such that the support portion is between the distal tip and the tissue wall; and
causing the expansion member to exert a proximal force against the tissue wall by exerting a proximal force on the elongated body when the expansion member is radially expanded outward.

19. The guide wire system of claim 1, wherein a difference between the cross-sectional dimension defined by the distal portion and the initial dimension is less than or equal to 20% of the initial dimension.

20. The guide wire system of claim 19, wherein the elongated body defines a longitudinal axis extending within the inner lumen at least through the support portion, and wherein the initial dimension and cross-sectional dimension are perpendicular to the longitudinal axis.

* * * * *